United States Patent
Govari et al.

(10) Patent No.: US 11,020,178 B2
(45) Date of Patent: Jun. 1, 2021

(54) SIMULTANEOUS CONTROL OF POWER AND IRRIGATION DURING ABLATION

(71) Applicant: Biosense Webster (Israel) Ltd., Yokneam (IL)

(72) Inventors: Assaf Govari, Haifa (IL); Andres Claudio Altmann, Haifa (IL); Ella Ozeri, Binyamina (IL); Israel Zilberman, Yokneam (IL)

(73) Assignee: Biosense Webster (Israel) Ltd., Yokneam (IL)

( * ) Notice: Subject to any disclaimer, the term of this patent is extended or adjusted under 35 U.S.C. 154(b) by 268 days.

(21) Appl. No.: 15/895,787

(22) Filed: Feb. 13, 2018

(65) Prior Publication Data

US 2018/0263689 A1 Sep. 20, 2018

Related U.S. Application Data

(60) Provisional application No. 62/470,940, filed on Mar. 14, 2017.

(51) Int. Cl.
*A61B 18/14* (2006.01)
*A61B 18/12* (2006.01)
*A61B 18/00* (2006.01)

(52) U.S. Cl.
CPC ...... *A61B 18/1492* (2013.01); *A61B 18/1206* (2013.01); *A61B 2018/00029* (2013.01);
(Continued)

(58) Field of Classification Search
CPC ...... A61B 18/1492; A61B 2018/00029; A61B 2018/00577; A61B 2018/00642
See application file for complete search history.

(56) References Cited

U.S. PATENT DOCUMENTS

2010/0168736 A1 7/2010 Wang
2011/0077626 A1 3/2011 Baerveldt et al.
(Continued)

FOREIGN PATENT DOCUMENTS

EP         2 742 891 A1    6/2014
WO    WO 2011/139589 A2   11/2011

OTHER PUBLICATIONS

European Search Report dated Jun. 21, 2018 from corresponding European Patent Application No. 18161397.7.

*Primary Examiner* — Nathan R Price
*Assistant Examiner* — Dung T Ulsh

(57) ABSTRACT

Apparatus, consisting of a probe configured to be inserted into contact with a myocardium, and an electrode attached to the probe. A temperature sensor, incorporated in the probe, is configured to output a temperature signal. A pump irrigates the myocardium, via the probe, with an irrigation fluid at a controllable rate, and a radiofrequency (RF) signal generator applies RF power via the electrode to the myocardium, so as to ablate the myocardium. The apparatus also has processing circuitry that measures a temperature of the probe, based on the temperature signal, while the RF power is applied and, when the measured temperature exceeds a preset target temperature, iteratively reduces the RF power applied by the signal generator and concurrently iteratively varies a rate of irrigation of the irrigation fluid provided by the pump, until the measured temperature is reduced to the preset target temperature.

8 Claims, 8 Drawing Sheets

(52) U.S. Cl.
CPC ............... *A61B 2018/00351* (2013.01); *A61B 2018/00577* (2013.01); *A61B 2018/00642* (2013.01); *A61B 2018/00702* (2013.01); *A61B 2018/00744* (2013.01); *A61B 2018/00791* (2013.01); *A61B 2018/00875* (2013.01); *A61B 2218/002* (2013.01)

(56) References Cited

U.S. PATENT DOCUMENTS

| | | | |
|---|---|---|---|
| 2012/0165812 A1* | 6/2012 | Christian | A61B 18/1492 606/41 |
| 2012/0165821 A1* | 6/2012 | Carignan | A61F 2/4657 606/89 |
| 2013/0267779 A1 | 10/2013 | Woolford et al. | |
| 2015/0238251 A1 | 8/2015 | Shikhman et al. | |

\* cited by examiner

SIMULTANEOUS CONTROL OF POWER AND IRRIGATION DURING ABLATION

CROSS-REFERENCE TO RELATED APPLICATION

This application claims the benefit of U.S. Provisional Patent Application 62/470,940, filed Mar. 14, 2017, which is incorporated herein by reference.

FIELD OF THE INVENTION

This invention relates generally to an ablative medical device, and specifically to control of parameters used during ablation performed by the device.

BACKGROUND OF THE INVENTION

Ablation of tissue, such as ablation performed by injecting radiofrequency (RF) power into the tissue, is a well-known procedure that is used in cardiac surgery where it is used to correct defects in the heart. Typically, in these cases the ablation is used to inactivate selected groups of cells in the myocardium, so that they no longer transfer an electro-potential wave in the myocardium.

SUMMARY OF THE INVENTION

An embodiment of the present invention provides apparatus, having a probe configured to be inserted into contact with a myocardium, and an electrode attached to the probe. A temperature sensor is incorporated in the probe and is configured to output a temperature signal. The apparatus also has a pump that is configured to irrigate the myocardium, via the probe, with an irrigation fluid at a controllable rate. A radiofrequency (RF) signal generator is configured to apply RF power via the electrode to the myocardium, so as to ablate the myocardium. The apparatus further includes processing circuitry that is configured to measure a temperature of the probe, based on the temperature signal, while the RF power is applied and, when the measured temperature exceeds a preset target temperature, iteratively reduce the RF power applied by the signal generator and concurrently iteratively vary a rate of irrigation of the irrigation fluid provided by the pump, until the measured temperature is reduced to the preset target temperature.

Typically, the circuitry, when the measured temperature does not exceed the preset target temperature, iteratively increases the RF power until the measured temperature is equal to the preset target temperature.

In a disclosed embodiment the controllable rate includes an idle irrigation rate and a high irrigation rate greater than the idle irrigation rate, and varying the rate of irrigation includes reducing the rate by pulsing the rate from the high irrigation rate to the idle irrigation rate and returning to the high irrigation rate. The disclosed embodiment may include tubing, attached to the probe, wherein pulsing the rate includes the tubing receiving a single pulse of the irrigation fluid at the idle irrigation rate and smoothing the rate of irrigation at the probe to be 50% of the high irrigation rate.

In a further disclosed embodiment the controllable rate includes an idle irrigation rate and a high irrigation rate greater than the idle irrigation rate, and varying the rate of irrigation includes increasing the rate by pulsing the rate from the idle irrigation rate to the high irrigation rate and returning to the idle irrigation rate. The further disclosed embodiment may include tubing, attached to the probe, wherein pulsing the rate includes the tubing receiving a single pulse of the irrigation fluid at the high irrigation rate and smoothing the rate of irrigation at the probe so that the rate increases by between 50% and 100% of the idle irrigation rate.

In a yet further disclosed embodiment the controllable rate includes an idle irrigation rate and a high irrigation rate greater than the idle irrigation rate, and the circuitry, when the measured temperature is less than a low target temperature below the preset target temperature, is configured to reduce the rate of irrigation from the high irrigation rate to the idle irrigation rate.

In an alternative embodiment the circuitry, when the measured temperature is between the preset target temperature and the low target temperature, is configured to maintain the rate of irrigation at the high irrigation rate.

There is further provided, according to an embodiment of the present invention, a method, consisting of:
inserting a probe into contact with a myocardium;
attaching an electrode to the probe;
incorporating a temperature sensor in the probe;
irrigating the myocardium, via the probe, with an irrigation fluid at a controllable rate;
applying radiofrequency (RF) power via the electrode to the myocardium, so as to ablate the myocardium;
measuring a temperature of the probe while the RF power is applied, using the temperature sensor; and, when the measured temperature exceeds a preset target temperature, iteratively reducing the RF power and concurrently iteratively varying a rate of irrigation of the irrigation fluid until the measured temperature is reduced to the preset target temperature.

The present disclosure will be more fully understood from the following detailed description of the embodiments thereof, taken together with the drawings, in which:

DETAILED DESCRIPTION OF EMBODIMENTS

Overview

During an ablation procedure the ablative power injected into cells needs to be well regulated, since if too little ablative energy is absorbed by the cells they may only partly inactivate, while if too much ablative energy is absorbed it may cause irreversible trauma to the heart. Another consideration for the power injected is the overall time for any given ablation procedure. Physicians typically prefer to keep the time to a minimum, so that in order to inject sufficient energy, the power injected during this time should be high. Thus, a goal for ablative power delivery is that the power level should be as high as possible, subject to not causing trauma.

To achieve this goal embodiments of the present invention provide apparatus, comprising a probe configured to be inserted into contact with a myocardium, an electrode attached to the probe, and a temperature sensor incorporated in the probe. The apparatus also comprises an irrigation module configured to irrigate the myocardium, via the probe, with an irrigation fluid at a controllable rate, and an ablation module configured to apply radiofrequency (RF) power via the electrode to the myocardium, so as to ablate the myocardium. The apparatus also has a temperature module configured, using the temperature sensor, to measure a temperature of the probe while the RF power is applied, and a processor, configured to operate the modules. When the measured temperature exceeds a preset target temperature, the processor iteratively reduces the RF power and concurrently iteratively varies a rate of irrigation of the irrigation fluid, until the measured temperature is reduced to the preset target temperature.

Tissue irrigation is necessary during ablation of the myocardium, to prevent problems such as tissue charring, or steam-pops occurring during the ablation. Legacy ablation systems typically provide irrigation at one of two rates—a low irrigation rate which, inter alia, may be used to maintain irrigation channels clear, and a high rate, which is used to prevent the problems referred to above. However, the high rate may lead to the tissue being overcooled, and in this case ablation power must be delivered for a longer-than-optimal time to correctly ablate the tissue.

An embodiment of the present invention solves the longer-than-optimal time delivery of legacy ablation systems by pulsing the irrigation rate between the low and high rates in a controlled manner. (The controlled pulsing has a similar effect to that of pulse width modulation for electronic systems.) In some embodiments of the present invention the pulsatory irrigation rate is smoothed, by tubing used to supply the irrigation fluid, so that the irrigation rate at the tissue is substantially constant. In addition, by varying the rate at which high rate pulses are applied, the smoothed irrigation rate may be varied in a substantially continuous manner between the low rate and the high rate.

DETAILED DESCRIPTION

Figure 1:
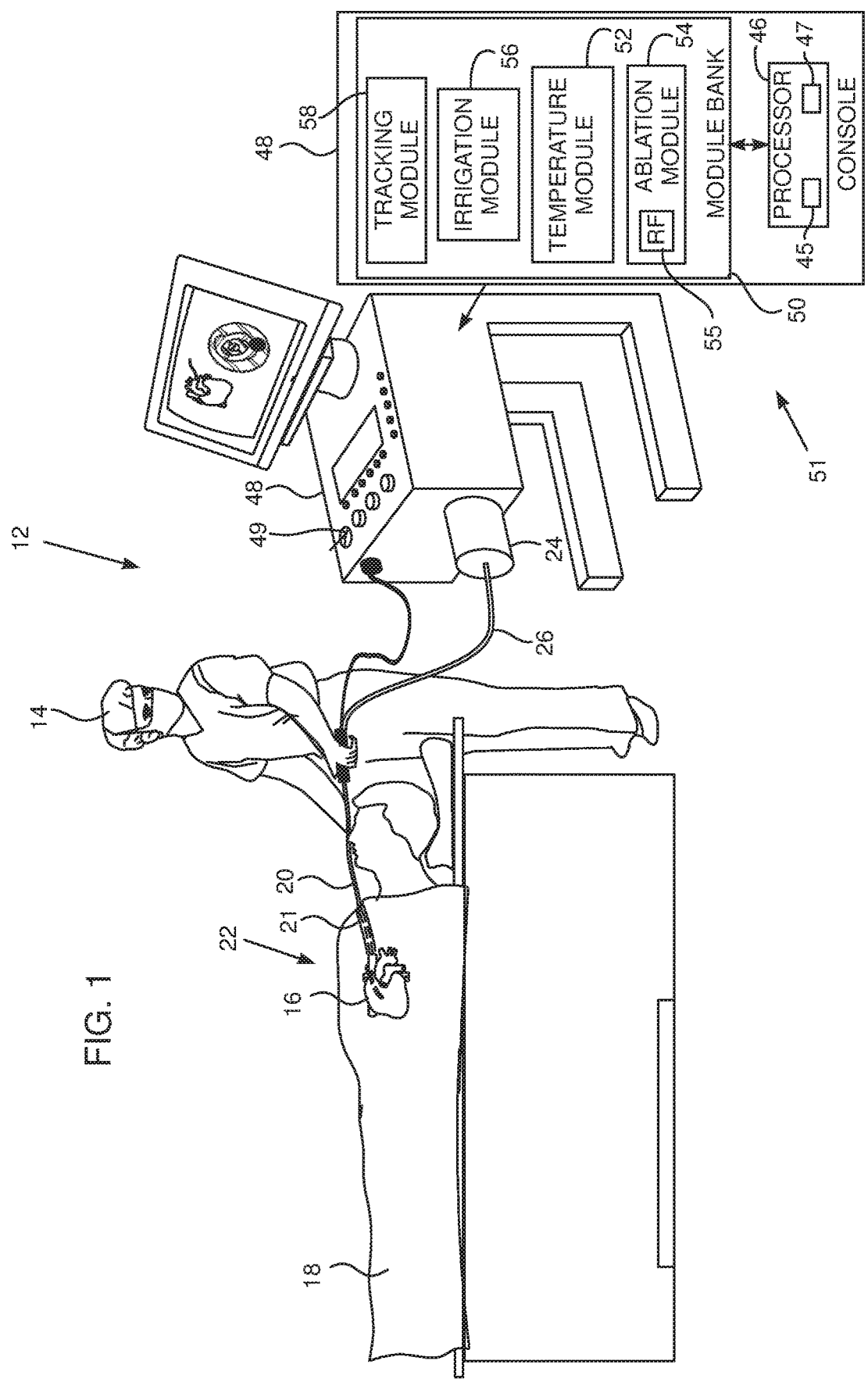
FIG. 1 is a schematic illustration of an invasive medical procedure using an apparatus, according to an embodiment of the present invention.
Figure 2:
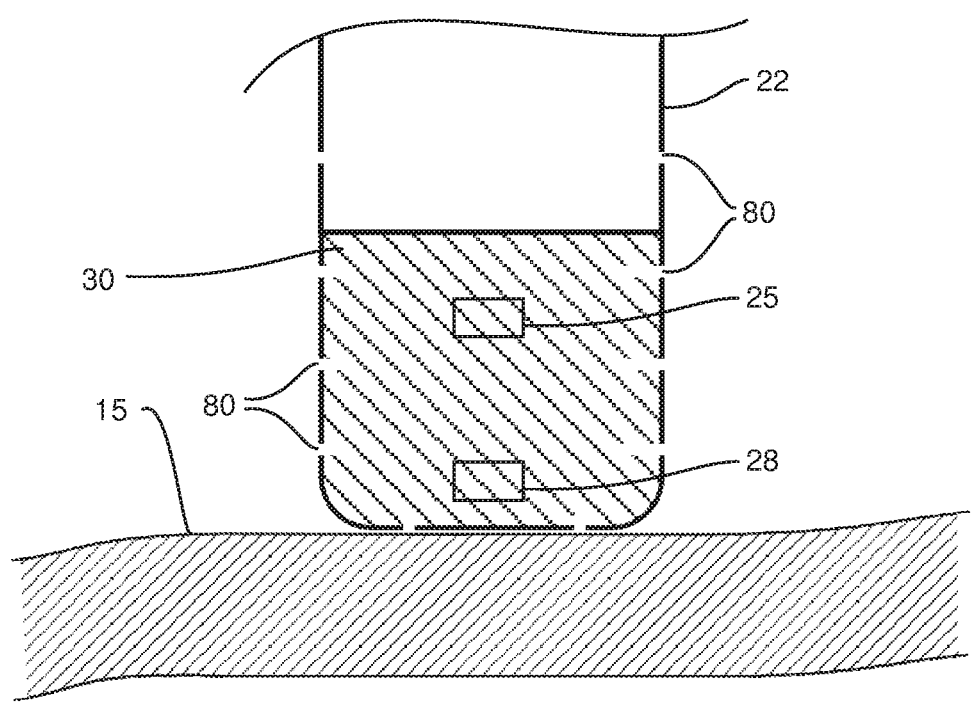
FIG. 2 is a schematic illustration of a distal end of a probe used in the apparatus, according to an embodiment of the present invention.

FIG. 1 is a schematic illustration of an invasive medical procedure using apparatus 12, and FIG. 2 is a schematic illustration of a distal end 22 of a probe 20 used in the apparatus, according to an embodiment of the present invention. The procedure is performed by a medical professional 14, and, by way of example, the procedure in the description hereinbelow is assumed to comprise ablation of a portion 15 of a myocardium 16 of the heart of a human patient 18. However, it will be understood that embodiments of the present invention are not just applicable to this specific ablation procedure, and may include substantially any ablation procedure on biological tissue or on non-biological material.

In order to perform the ablation, professional 14 inserts a probe 20 into a sheath 21 that has been pre-positioned in a lumen of the patient. Sheath 21 is positioned so that distal end 22 of the probe may enter the heart of the patient, after exiting a distal end of the sheath, and contact tissue of the heart. Distal end 22 comprises a position sensor 25 that enables the location and orientation of the distal end to be tracked, and one or more temperature sensors 28 that measure the temperature at respective locations of the distal end. Distal end 22 also comprises an electrode 30 which is used to deliver radiofrequency ablation power to myocardium 16 in order to ablate the myocardium. (Electrode 30 may also be used to acquire electropotentials from the myocardium, as noted below.)

Apparatus 12 is controlled by a system processor 46 which comprises real-time noise reduction circuitry 45, typically configured as a field programmable gate array (FPGA), followed by an analog-to-digital (A/D) signal conversion integrated circuit 47. The processor can pass the signals from A/D circuit 47 to modules described herein, and/or another processor and/or can be programmed to perform at least one of the algorithms disclosed herein, the algorithms comprising steps described hereinbelow. The processor uses circuitry 45 and circuit 47, as well as features of the modules referred to above, in order to perform the algorithms. Processor 46 and the modules operated by the processor are herein termed processing circuitry 51.

Processor 46 is located in an operating console 48 of the apparatus. Console 48 comprises controls 49 which are used by professional 14 to communicate with processor 46, and to implement the procedure the processor communicates with modules in a module bank 50. Modules in bank 50 are described below.

During the procedure performed by professional 14, distal end 22 is supplied with irrigation fluid, typically normal saline solution, from a pump 24, and the pump transfers the fluid to probe 20 via irrigation tubing 26. The irrigation fluid is expelled through irrigation holes 80 in the distal end.

Except as stated below, pump 24 is assumed to be able to operate in one of two modes: an idle mode, wherein the pump pumps the irrigation fluid at a slow rate, also herein termed an idle rate, and a full flow mode, wherein the pump pumps the fluid at a fast rate, also herein termed a full flow rate. Each of the rates may be preset before the pump is used in apparatus 12, and in one embodiment the idle rate may be set within a range of 0-6 mL/min, and the full rate may be set within a range of 6-60 mL/min.

In some embodiments the flow rate from pump 24 may be continuously adjusted by using a PID (proportional integral derivative) algorithm to control the flow rate according to the radiofrequency ablation power delivered. For simplicity and clarity, the description hereinbelow assumes that pump 24 operates in one of the two modes (an idle mode or a full flow mode) described above, and those of ordinary skill in the art will be able to adapt the description, mutatis mutandis, if the flow from the pump can be continually adjusted.

As stated above, in order to operate apparatus 12, processor 46 communicates with module bank 50. Thus, bank 50 comprises a tracking module 58 which receives and analyzes signals from position sensor 25, and which uses the signal analysis to generate a location and an orientation of distal end 22. In some embodiments sensor 25 comprises one or more coils which provide the sensor signals in response to magnetic fields traversing the coils. In these embodiments, in addition to receiving and analyzing signals from sensor 25, tracking module 58 also controls magnetic radiators (not shown in the figures) which radiate the magnetic fields traversing sensor 25. The radiators are positioned in proximity to myocardium 16, and are configured to radiate alternating magnetic fields into a region in proximity to the myocardium.

Alternatively or additionally, tracking module 58 may measure impedances between electrode 80 and electrodes (not shown in the figures) on the surface of patient 18, and processor 46 and the tracking module may use the impedances to track the location and orientation of distal end 22. The Carto® system produced by Biosense Webster, of 33 Technology Drive, Irvine, Calif. 92618 USA, uses such a magnetic tracking system and an impedance tracking system.

As explained in more detail below, an irrigation module 56 controls the rate of flow of the fluid from pump 24, by switching between the two modes of operation of the pump. Irrigation module 56 is under overall control of processor 46.

Processor 46 uses a temperature module 52 to analyze signals received from one or more temperature sensors 28 in distal end 22. From the analyzed signals, processor 46 determines temperatures of the distal end, and uses the temperatures in the algorithms described below.

Module bank 50 also comprises an ablation module 54. Ablation module 54 comprises a radiofrequency (RF) generator 55, which enables processor 46 to inject RF current, via electrode 80 of the distal end and one or more returning electrodes (not shown in the figures) on the skin of the patient, into myocardium 16, in order to ablate regions of the myocardium which are in contact with the electrode. The ablation module also enables the processor to set parameters of the injected current, such as its frequency, the level of the power injected, and the duration of the injection.

In embodiments of the present invention, the level of the power injected may be provided to ablation module 54 by professional 14 as an ablation target power, which is a maximum power that may be injected into the patient's tissue by electrode 80. Typically the ablation target power is set within an approximate range of 20 W-70 W, although the ablation target power may be set outside this range.

In embodiments of the present invention apparatus 12 is configured to operate in one of two power modes. In a low power mode, the ablation target power is set to be less than or equal to a preset power level. In a high power mode the ablation target power is set to be greater than the preset power level. By way of example, in the description herein the preset power level is assumed to be 35 W. However, it will be understood that the preset power level, separating the two power modes, may be higher or lower than 35 W.

The software for processor 46 and module bank 50 may be downloaded to the processor in electronic form, over a network, for example. Alternatively or additionally, the software may be provided on non-transitory tangible media, such as optical, magnetic, or electronic storage media.

In order to operate apparatus 12, module bank 50 typically comprises modules other than those described above, such as a force module which acquires signals from a force sensor in the distal end and which analyzes the signals to determine a force on the distal end. For simplicity, such other modules and their associated sensors are not illustrated in FIG. 1. All modules may comprise hardware as well as software elements.

Figure 3:
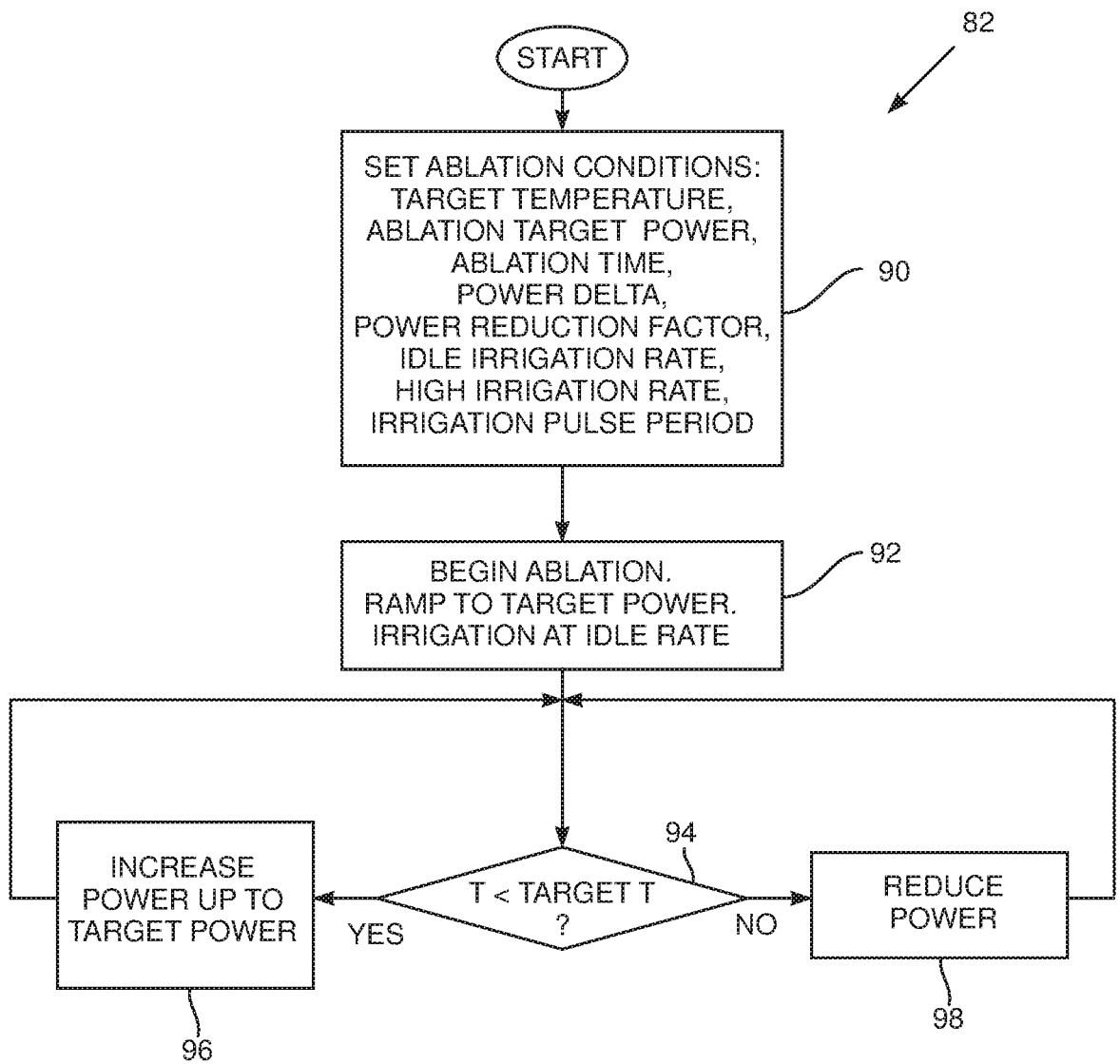
FIG. 3 is a first flowchart of steps comprised in an algorithm used by the apparatus, according to an embodiment of the present invention.
Figure 4:
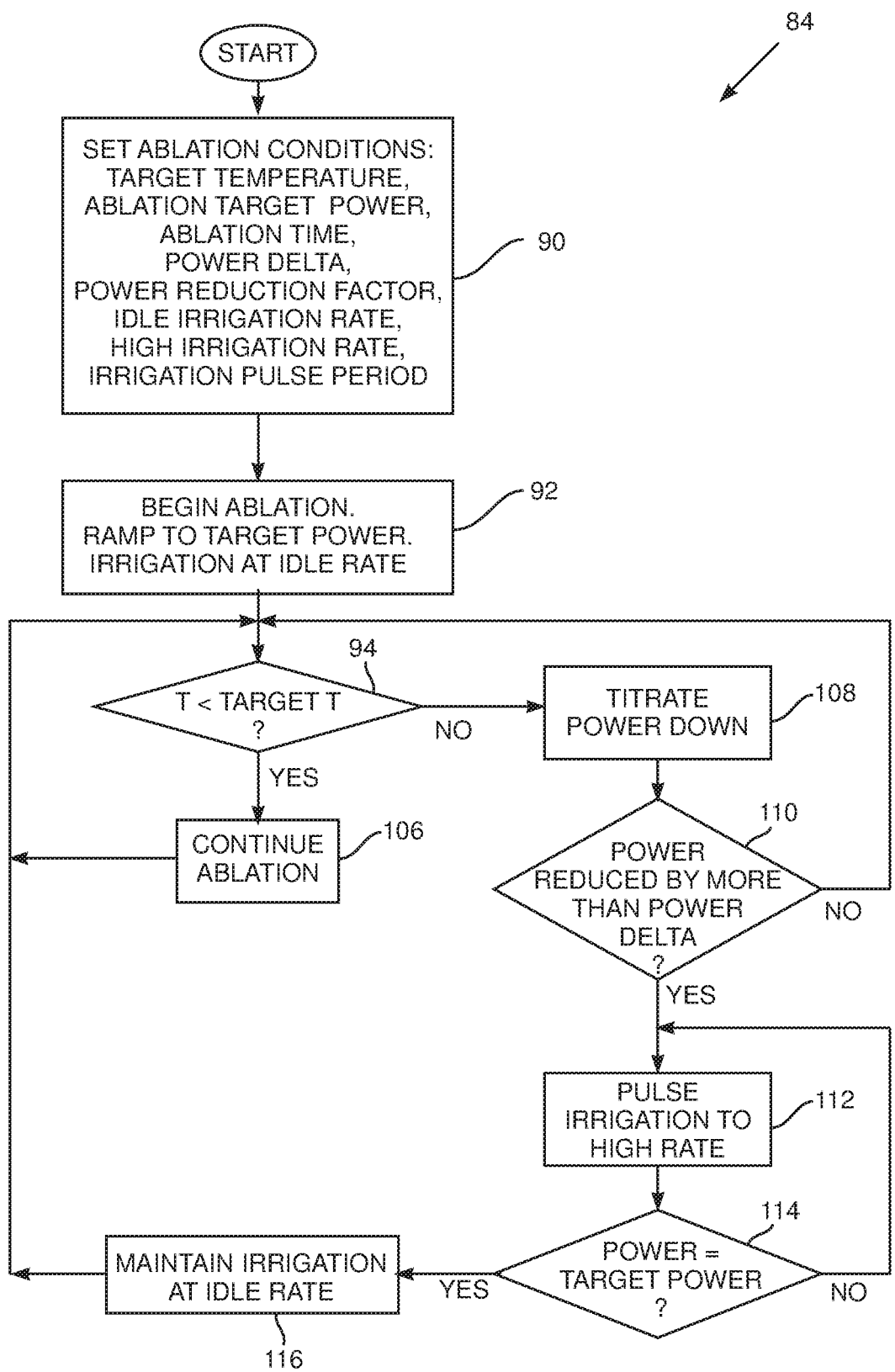
FIG. 4 is a second flowchart of steps comprised in the algorithm used by the apparatus, according to an embodiment of the present invention.

FIG. 3 is a first flowchart of steps of an algorithm followed by processor 46 when apparatus 12 is operating in the low power mode described above, while professional 14 performs the ablation procedure referred to above, and FIG. 4 is a second flowchart of steps of the algorithm followed by the processor, according to an embodiment of the present invention. As is described below, in the first flowchart, also referred to herein as flowchart 82, the processor varies the power, and in the second flowchart, also referred to herein as flowchart 84, the processor varies the irrigation rate. The processor operates both flowcharts concurrently.

In the first flowchart (FIG. 3) in an initial step 90, typically performed prior to the actual ablation, the professional uses controls 49 to assign values to parameters used by the processor in performing the algorithm.

Typical parameters set in the initial step comprise:

A target temperature, as measured as an average of sensors 28, which is an upper threshold temperature for performance of the ablation. In a disclosed embodiment the target temperature is set at 55° C., although the target temperature may typically be set in a range from 50° C. to 60° C., or outside this range of values.

The ablation target power, which, as stated above, is a maximum power that may be injected into the patient's tissue by electrode 80. Ablation module 54 uses the ablation target power value to ensure that the injected power does not exceed this value. For the descriptions herein of the flowcharts of FIG. 3 and FIG. 4, the ablation target power is assumed to be set at 35 W, so that apparatus 12 is operating in its low power mode.

An ablation time, which is a maximum overall time period, used by ablation module 54, for which a single ablation is performed. In a disclosed embodiment the ablation time is set at 60 s.

A power delta, which is a change in power that the processor checks in evaluating a condition in the algorithm. In a disclosed embodiment the power delta is set at 1 W. A typical range for the power delta is 0.5 W-5 W.

A power reduction factor, which is a reduction in power that the processor implements when titrating the power to a lower value. In a disclosed embodiment the power reduction factor is set at 0.1 W. A typical range for the reduction factor is 0.05 W-0.2 W.

An idle irrigation flow rate, which is the flow rate of pump 24 when the irrigation module sets the pump to operate in its idle mode. A typical range for the idle irrigation flow rate is 1 mL/min-5 mL/min, and in a disclosed embodiment the rate is set at 4 mL/min.

A high irrigation flow rate, which is the flow rate of pump 24 when the irrigation module sets the pump to operate in its full flow mode. A typical range for the high irrigation flow rate is 6 mL/min-60 mL/min, and in a disclosed embodiment the rate is set at 15 mL/min.

An irrigation pulse period, which is the period of time in which the irrigation module pulses the pump to toggle from its idle mode, to the full flow mode, then return to the idle mode, or alternatively, to toggle from its full flow mode, to the idle mode, then return to the full flow mode. In a disclosed embodiment the irrigation pulse period is 0.5 s, and the period may typically range between 0.1 s and 2 s.

Once the parameters have been set in step 90, control of the algorithm proceeds to a begin ablation step 92, wherein the processor ramps the power dissipated by electrode 80 up to the target power level set in step 90. Depending whether the target power level sets the apparatus to operate in the low power mode or the high power mode, the irrigation rate is set accordingly, i.e., for the low power mode at the low irrigation rate, and for the high power mode at the high irrigation rate. Since, as stated above, the target power level is set in step 90 at 35 W, corresponding to the low power mode, then in step 92 the irrigation rate is set at the idle irrigation flow rate.

In a condition 94, the processor uses temperature module 52 to check if the maximum temperature measured by any one of sensors 28 is lower than the target temperature set in step 90. Condition 94 iterates at a preset rate, which in an embodiment of the present invention is every 33 ms.

If condition 94 returns positive, i.e., if the temperature is less than the target temperature, then in an increase power step 96 processor 46 uses the ablation module to increase the power, typically by the same value as the power reduction factor set in step 90, up to the target power.

If condition 94 returns negative, then in a decrease power step 98 processor 46 uses the ablation module to decrease the power by the power reduction factor. Further details of the power decrease are described in flowchart 84 (FIG. 4).

In flowchart 84 the initial steps of the flowchart, steps 90, 92, and 94, are as described above with reference to flowchart 82 (FIG. 3). If in flowchart 84 condition 94 returns positive, i.e., the maximum temperature is less than the target temperature, then in a continuing ablation step 106 the processor continues with the ablation, and control returns to condition 94.

If condition 94 returns negative, i.e., the maximum temperature is equal to or greater than the target temperature, then in a power titration step 108 the processor uses ablation module 54 to titrate the power level down by the preset reduction factor set in step 90. Control then continues to a second condition 110.

In second condition 110, the processor interrogates ablation module 54 to find the level of power being injected into electrode 80, and the processor checks if the level has been reduced by more than the power delta set in step 90. If the second condition returns negative, i.e., the power has not been reduced from the target power value by the power delta, control returns to condition 94, which continues to iterate at its preset rate.

If second condition 110 returns positive, i.e., the power has been reduced from the target power value by more than the power delta, control of the algorithm continues to an irrigation pulse step 112. In step 112 irrigation module 56 configures pump 24 to transfer from its idle mode, i.e., pumping at the idle rate set in step 90, to its full flow mode wherein the pump pumps the irrigation fluid at its high rate set in step 90. The transfer to the full flow mode continues for the irrigation pulse period set in step 90, after which module 56 returns pump 24 to pumping at its idle rate.

At the conclusion of step 112, control continues to a third condition 114, wherein the processor checks if the power set in flowchart 82 (FIG. 3), is equal to the target power.

If condition 114 returns positive, i.e., the power is equal to the target power, then in a further continuing ablation step 116 the processor uses the irrigation module to maintain the irrigation rate at the idle rate, and transfers control back to first condition 94.

If condition 114 returns negative, i.e., the power has not returned to the target power, then control returns to irrigation pulse step 112, so that the irrigation rate again pulses to a high rate.

Processor 46 continues implementing the steps of the two flowcharts 82, 84 concurrently for the ablation time set in step 90, after which the implementation ceases.

Figure 5:
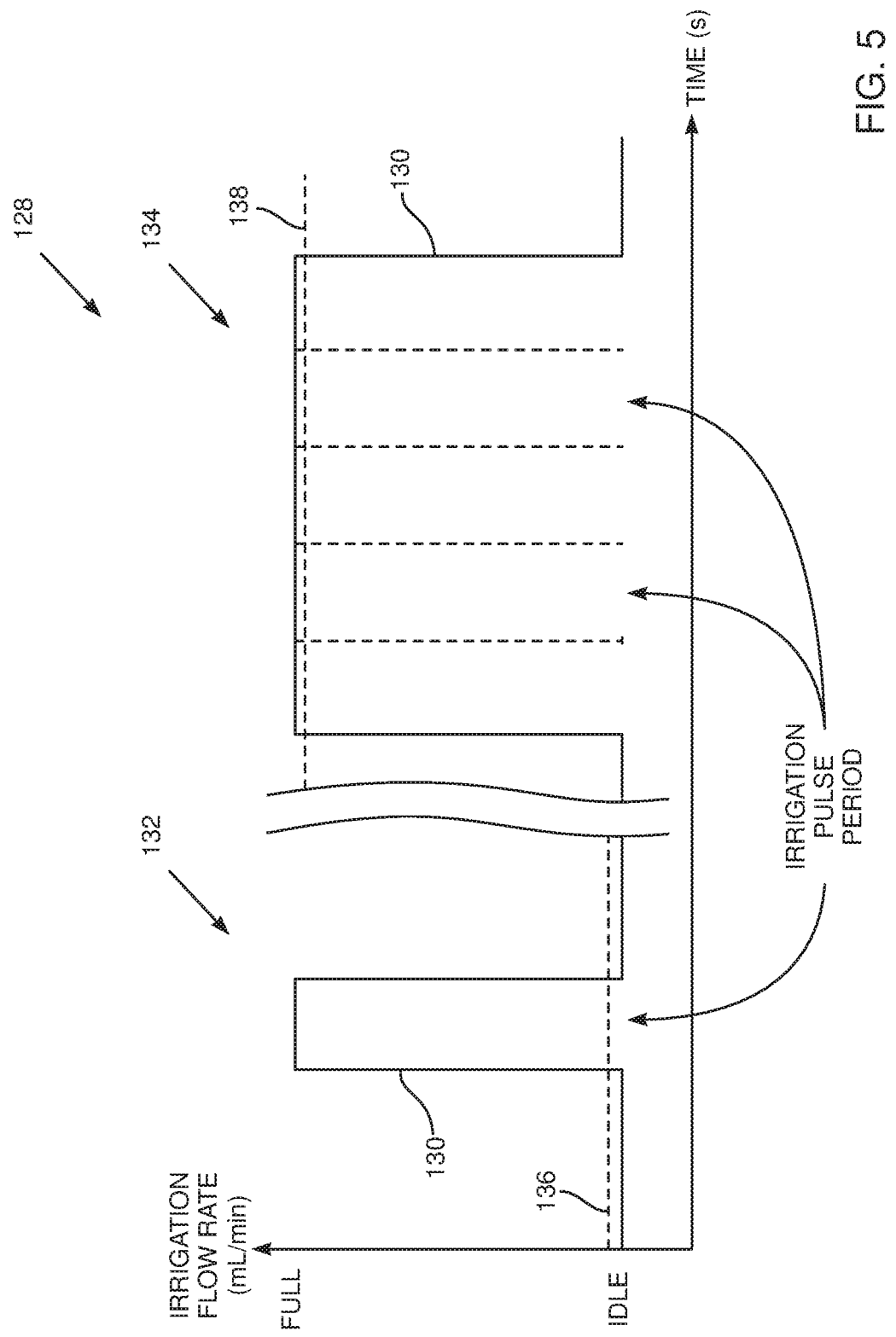
FIG. 5 illustrates graphically the operation of a pump of the apparatus while the flowcharts of FIGS. 3 and 4 are operative, according to an embodiment of the present invention.

FIG. 5 illustrates graphically the operation of pump 24 while flowcharts 82, 84 are operative, according to an embodiment of the present invention. A graph 128 plots irrigation flow rate vs. time, and a solid line 130 of the graph illustrates the output flow rate of pump 24.

A section 132 of graph 128 illustrates the flow rate from pump 24, as solid line 130, as flowchart 84 proceeds to step 112, and then continues via condition 114, which returns positive, to step 116. In this case condition 114 is addressed only once, so that the flow rate from the pump begins at the idle rate, pulses for one irrigation pulse period to the high rate and then returns to the idle rate.

A section 134 of graph 128 illustrates the flow rate from pump 24, as solid line 130, as flowchart 84 proceeds to step 112, and then continues to condition 114, which returns negative, so returning to step 112. In this case condition 114 iterates, so that while the flow rate from the pump begins at the idle rate, the flow rate from the pump continues with multiple pulses, that present as effectively one long pulse, at the high rate.

As stated above solid line 130 illustrates the output of pump 24. However, the pulsatory output from the pump is smoothed, or averaged, by irrigation tubing 26, and the smoothed output is illustrated schematically by a broken line 136 for section 132, and a broken line 138 for section 134. The smoothed output is the irrigation flow rate at distal end 22.

For the irrigation pulse period of 0.5 s of the disclosed embodiment referred to above, one pulse at a high rate of 15 mL/min, during an idle rate of 4 mL/min, typically increases the irrigation rate by between 50% and 100% of the idle rate, i.e., to an effective smoothed irrigation rate between 6 mL/min and 8 ml/min. A train of two or more pulses typically increases the effective irrigation rate to the high rate.

It will be understood that by varying the rate of pulsation of pump 24, and due to the smoothing effect of tubing 26, the irrigation flow rate at distal end 22 can be varied substantially continuously between the idle irrigation rate and the high irrigation rate.

Figure 6:
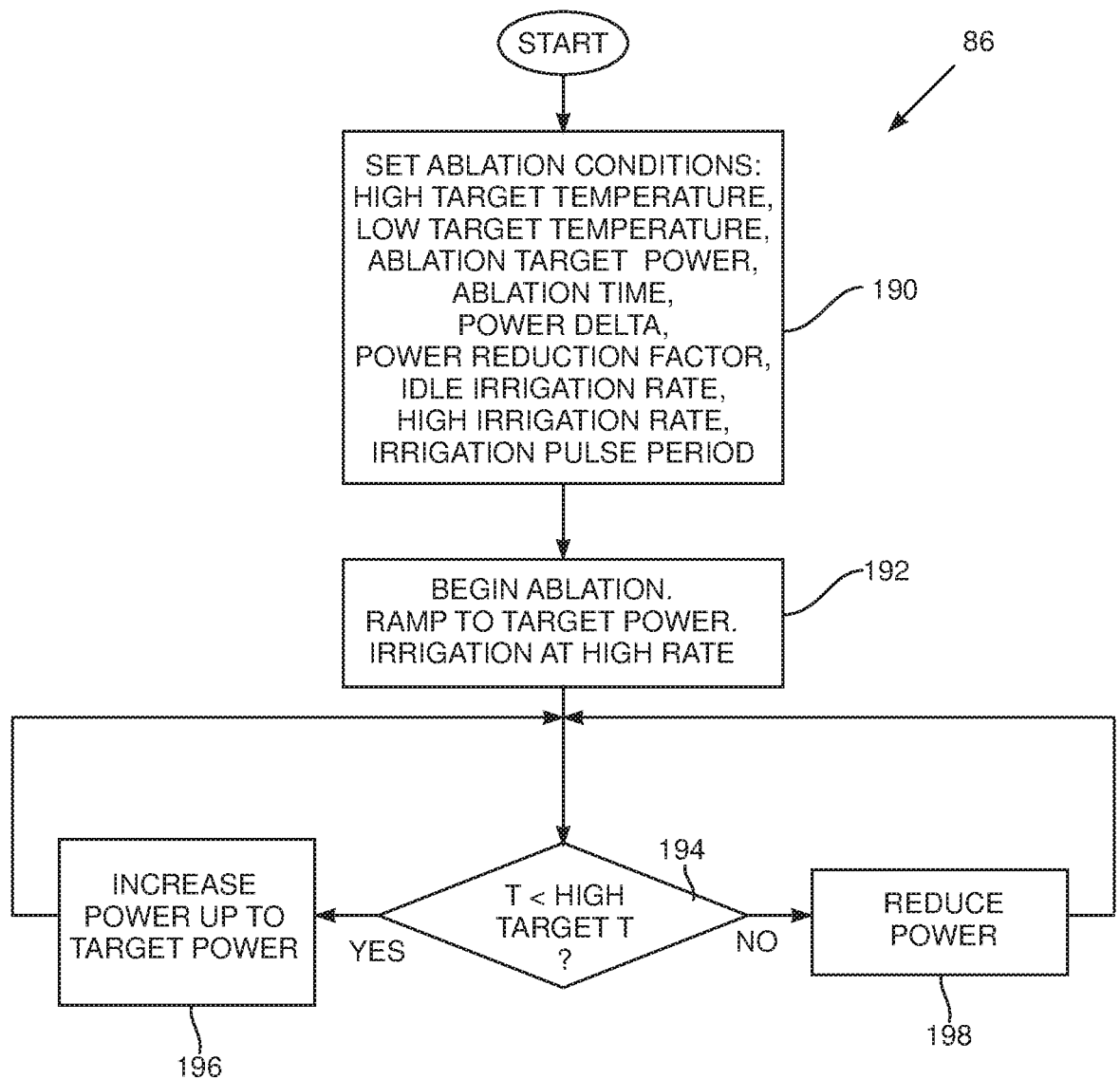
FIG. 6 is a first flowchart of steps of an alternative algorithm used by the apparatus, according to an embodiment of the present invention.
Figure 7:
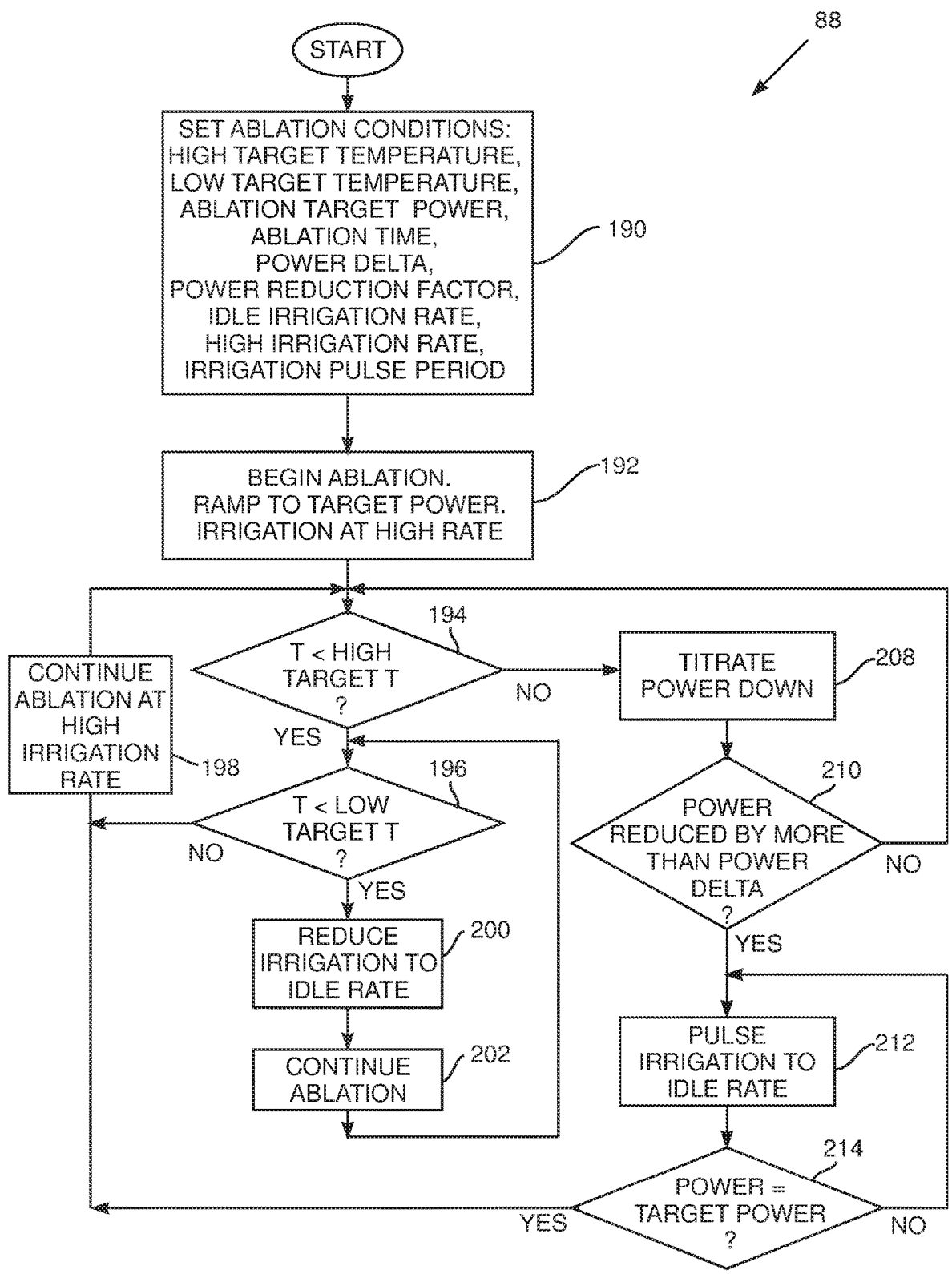
FIG. 7 is a second flowchart of steps of the alternative algorithm, according to an embodiment of the present invention.

FIG. 6 is a first flowchart of steps of an alternative algorithm followed by processor 46 when apparatus 12 is operating in the high power mode referred to above, while professional 14 performs the ablation procedure, and FIG. 7 is a second flowchart of steps of the alternative algorithm followed by the processor, according to an embodiment of the present invention. The flowchart of FIG. 6 is also referred to herein as flowchart 86, and the flowchart of FIG. 7 is also referred to herein as flowchart 88.

As for flowcharts 82 and 84 (FIG. 3 and FIG. 4), in flowchart 86 (FIG. 6) the processor varies the power, and in flowchart 88 (FIG. 7) the processor varies the irrigation rate; the processor operates both flowcharts 86 and 88 concurrently.

An initial step 190 of flowchart 86 (FIG. 6) is substantially as described above for step 90, except that rather than setting one target temperature, a high target temperature and a low target temperature are set. The high target temperature is typically set to be in an approximate range of 40° C. to 55° C., although values outside this range are possible. The low target temperature is typically set to be in an approximate range of 37° C. to 50° C., although values outside this range are also possible. Regardless of the actual values of the high and low target temperatures, the low target temperature is set to be at least 1° C. less than the high target temperature. In a disclosed embodiment the high target temperature is set at 50° C. and the low target temperature is set at 45° C.

A condition 194 is substantially similar to condition 94, except that processor uses temperature module 52 to check if the maximum temperature measured by any one of sensors 28 is lower than the high target temperature.

If condition 194 returns positive, i.e., if the temperature is less than the high target temperature, then in an increase power step 196 processor 46 uses the ablation module to increase the power, typically by the same value as the power reduction factor set in step 190, up to the target power.

If condition 194 returns negative, then in a decrease power step 198 processor 46 uses the ablation module to decrease the power by the power reduction factor. Further details of the power decrease are described in flowchart 88.

In flowchart 88 (FIG. 7) the initial steps of the flowchart, steps 190, 192, and 194, are as described above with reference to flowchart 86. If in flowchart 88 condition 194 returns positive, i.e., the maximum temperature is less than the high target temperature, then control transfers to a further condition 196, where the processor checks if the maximum temperature is less than the low target temperature. Condition 196 typically iterates at the same preset rate as condition 194.

If condition 196 returns negative, so that the maximum temperature is between the low and high target temperatures, then control transfers to a continuing ablation step 198, wherein ablation is continued at the high irrigation rate set initially, and control returns to condition 194.

If condition 196 returns positive, so that the maximum temperature is below the low target temperature, then control transfers to a reduce irrigation step 200, where the processor reduces the high irrigation rate set initially to the idle irrigation rate. Ablation continues at the idle irrigation rate in a continuing ablation step 202 and control transfers back to iterating condition 196.

The path of condition 196, step 200, and step 202 illustrates that while the maximum temperature is below the low target temperature, the processor maintains the irrigation at its low idle rate.

Returning to condition 194, if the condition returns negative, i.e., the maximum temperature is equal to or greater than the high target temperature, then in a power titration step 208 the processor titrates the power down, substantially as described in power titration step 108. Control then continues to a power reduction condition 210.

Condition 210 is substantially as described for condition 110, i.e., the processor interrogates ablation module 54 to check if the power level has been reduced by more than the power delta set in step 190. If condition 210 returns negative, i.e., the power has not been reduced from the target power value by the power delta, control returns to condition 194, which continues to iterate at its preset rate.

If condition 210 returns positive, i.e., the power has been reduced from the target power value by more than the power delta, control of the algorithm continues to an irrigation pulse step 212. In step 212 irrigation module 56 configures pump 24 to transfer from its full flow mode, i.e., pumping at the high rate set in step 190, to its idle mode wherein the pump pumps the irrigation fluid at its low rate set in step 190. The transfer to the idle mode continues for the irrigation pulse period set in step 190, after which module 56 returns pump 24 to pumping at its full rate.

At the conclusion of step 212, control continues to a power check condition 214, wherein the processor checks if the power set in flowchart 86 (FIG. 6), is equal to the target power.

If condition 214 returns positive, i.e., the power is equal to the target power, then control continues at continuing ablation step 198, where the irrigation module maintains the irrigation rate at the full rate, and transfers control back to condition 194.

If condition 214 returns negative, i.e., the power has not returned to the target power, then control returns to irrigation pulse step 212, so that the irrigation rate again pulses to a low rate.

Processor 46 continues implementing the steps of the two flowcharts 82, 84 concurrently for the ablation time set in step 90, after which the implementation ceases.

Figure 8:
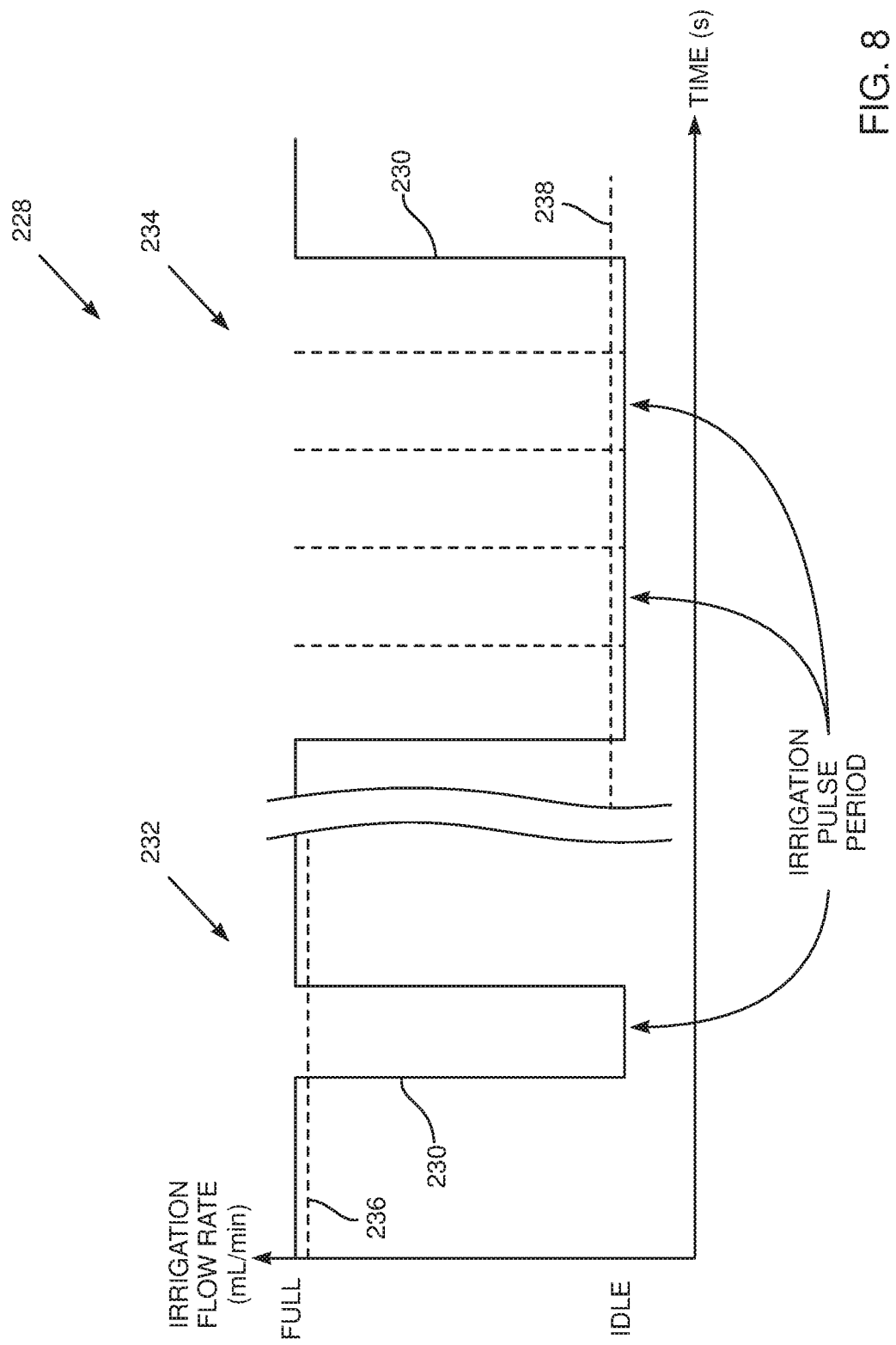
FIG. 8 illustrates graphically the operation of the pump of the apparatus while the flowcharts of FIGS. 6 and 7 are operative, according to an embodiment of the present invention.

FIG. 8 illustrates graphically the operation of pump 24 while flowcharts 86, 88 are operative, according to an embodiment of the present invention. A graph 228 plots irrigation flow rate vs. time, and a solid line 230 of the graph illustrates the output flow rate of pump 24.

A section 232 of graph 228 illustrates the flow rate from pump 24, as solid line 230, as flowchart 88 proceeds to step 212, and then continues via condition 214, which returns positive, to step 198. In this case condition 214 is addressed only once, so that the flow rate from the pump begins at the full rate, pulses for one irrigation pulse period to the low rate and then returns to the idle rate.

A section 234 of graph 228 illustrates the flow rate from pump 24, as solid line 230, as flowchart 88 proceeds to step 212, and then continues to condition 214, which returns negative, so returning to step 212. In this case condition 214 iterates, so that while the flow rate from the pump begins at the high rate, the flow rate from the pump continues with multiple pulses, that present as effectively one long pulse, at the low rate.

As stated above solid line 230 illustrates the output of pump 24. However, the pulsatory output from the pump is smoothed, or averaged, by irrigation tubing 26, and the smoothed output is illustrated schematically by a broken line 236 for section 232, and a broken line 238 for section 234. The smoothed output is the irrigation flow rate at distal end 22.

The smoothing is generally similar to that described above with respect to FIG. 5. Thus, for an irrigation pulse period of 0.5 s, a single pulse at an idle rate of 4 mL/min, during a high rate of 15 mL/min, typically reduces the irrigation rate by approximately 50% of the high rate, i.e., to approximately 8 mL/min. A train of two or more pulses typically reduces the effective irrigation rate to the idle rate.

It will be appreciated that the embodiments described above are cited by way of example, and that the present invention is not limited to what has been particularly shown and described hereinabove. Rather, the scope of the present invention includes both combinations and subcombinations of the various features described hereinabove, as well as variations and modifications thereof which would occur to persons skilled in the art upon reading the foregoing description and which are not disclosed in the prior art.

The invention claimed is:

1. Apparatus for simultaneous control of power and irrigation during ablation, the apparatus comprising:
a probe configured to be inserted into contact with a myocardium;
an electrode attached to the probe;
a temperature sensor incorporated in the probe and configured to output a temperature signal;
a pump configured to irrigate the myocardium, via the probe, with an irrigation fluid at a controllable rate;
a radiofrequency (RF) signal generator configured to apply RF power via the electrode to the myocardium, so as to ablate the myocardium; and processing circuitry configured to measure a temperature of the probe, based on the temperature signal, while the RF power is applied and, when the measured temperature exceeds a preset target temperature, iteratively reduce the RF power applied by the signal generator based upon a preset power delta and concurrently iteratively vary a rate of irrigation of the irrigation fluid provided by the pump at a preset iteration rate, until the measured temperature is reduced to the preset target temperature.

2. The apparatus according to claim 1, wherein the circuitry, when the measured temperature does not exceed the preset target temperature, iteratively increases the RF power until the measured temperature is equal to the preset target temperature.

3. The apparatus according to claim 1, wherein the controllable rate comprises an idle irrigation rate and a high irrigation rate greater than the idle irrigation rate, and wherein varying the rate of irrigation comprises reducing the rate by pulsing the rate from the high irrigation rate to the idle irrigation rate and returning to the high irrigation rate.

4. The apparatus according to claim 3, and comprising tubing, attached to the probe, and wherein pulsing the rate comprises the tubing receiving a single pulse of the irrigation fluid at the idle irrigation rate and smoothing the rate of irrigation at the probe to be 50% of the high irrigation rate.

5. The apparatus according to claim 1, wherein the controllable rate comprises an idle irrigation rate and a high irrigation rate greater than the idle irrigation rate, and wherein varying the rate of irrigation comprises increasing the rate by pulsing the rate from the idle irrigation rate to the high irrigation rate and returning to the idle irrigation rate.

6. The apparatus according to claim 5, and comprising tubing, attached to the probe, and wherein pulsing the rate comprises the tubing receiving a single pulse of the irrigation fluid at the high irrigation rate and smoothing the rate of irrigation at the probe so that the rate increases by between 50% and 100% of the idle irrigation rate.

7. The apparatus according to claim 1, wherein the controllable rate comprises an idle irrigation rate and a high irrigation rate greater than the idle irrigation rate, and wherein the circuitry, when the measured temperature is less than a low target temperature below the preset target temperature, is configured to reduce the rate of irrigation from the high irrigation rate to the idle irrigation rate.

8. The apparatus according to claim 7, wherein the circuitry, when the measured temperature is between the preset target temperature and the low target temperature, is configured to maintain the rate of irrigation at the high irrigation rate.

* * * * *